United States Patent
Magro et al.

(10) Patent No.: US 10,748,296 B2
(45) Date of Patent: Aug. 18, 2020

(54) METHODS AND DEVICES FOR SURFACE MOTION TRACKING

(71) Applicant: Elekta, Inc., Atlanta, GA (US)

(72) Inventors: Nicolette Patricia Magro, Maryland Heights, MO (US); Xiao Han, Maryland Heights, MO (US)

(73) Assignee: Elekta, Inc., Atlanta, GA (US)

( * ) Notice: Subject to any disclaimer, the term of this patent is extended or adjusted under 35 U.S.C. 154(b) by 58 days.

(21) Appl. No.: 15/874,511

(22) Filed: Jan. 18, 2018

(65) Prior Publication Data
US 2019/0220986 A1 Jul. 18, 2019

(51) Int. Cl.
| | |
|---|---|
| *G06T 7/38* | (2017.01) |
| *A61B 5/00* | (2006.01) |
| *A61B 5/01* | (2006.01) |
| *A61B 5/055* | (2006.01) |
| *A61B 6/03* | (2006.01) |
| *A61B 6/00* | (2006.01) |
| *A61N 5/10* | (2006.01) |
| *G06T 7/30* | (2017.01) |
| *A61B 90/00* | (2016.01) |

(52) U.S. Cl.
CPC .............. *G06T 7/38* (2017.01); *A61B 5/0077* (2013.01); *A61B 5/015* (2013.01); *A61B 5/055* (2013.01); *A61B 6/032* (2013.01); *A61B 6/4085* (2013.01); *A61N 5/1039* (2013.01); *G06T 7/30* (2017.01); *A61B 2090/364* (2016.02); *G06T 2207/10004* (2013.01); *G06T 2207/10021* (2013.01); *G06T 2207/10048* (2013.01); *G06T 2207/10081* (2013.01); *G06T 2207/10088* (2013.01); *G06T 2207/10108* (2013.01); *G06T 2207/20221* (2013.01); *G06T 2207/30004* (2013.01)

(58) Field of Classification Search
CPC ....... A61B 5/0077; A61B 5/015; A61B 5/055; A61B 6/032; A61B 6/4085
See application file for complete search history.

(56) References Cited

U.S. PATENT DOCUMENTS

| | | | | |
|---|---|---|---|---|
| 2017/0337682 | A1* | 11/2017 | Liao | ......................... G06T 7/30 |
| 2018/0046875 | A1* | 2/2018 | Caluser | ................ A61B 8/4245 |
| 2019/0000318 | A1* | 1/2019 | Caluser | ................ A61B 5/0035 |

FOREIGN PATENT DOCUMENTS

WO     WO-2019143684 A1     7/2019

OTHER PUBLICATIONS

Lee et al. "Automatic Marker-free Longitudinal Infrared Image Registration by Shape Context Based Matching and Competitive Winner-guided Optimal Corresponding" Feb. 1, 2017 (16 pages).

(Continued)

*Primary Examiner* — Kim Y Vu
*Assistant Examiner* — Molly Delaney
(74) *Attorney, Agent, or Firm* — Schwegman Lundberg & Woessner, P.A.; Sanjay Agrawal

(57) ABSTRACT

Embodiments of the disclosure may be directed to an image processing system configured to receive a medical image of a region of a subject's body taken at a first time and to receive a surface image of an exterior portion of the region of the subject's body taken at the first time. The image processing may also be configured to receive a medical image of the region of the subject's body taken at a second time and to register the medical image taken at the first time, the surface image taken at the first time, and the medical image taken at the second time.

15 Claims, 8 Drawing Sheets

(56) References Cited

OTHER PUBLICATIONS

Bichinho et al. "A Computer Tool for the Fusion and Visualization of Thermal and Magnetic Resonance Images" vol. 22, No. 5 Oct. 2009: pp. 527-534 (8 pages).
Yasas et al. "How Accurate Are the Fusion of Cone-Beam CT and 3-D Stereophotographic Images?" Nov. 2012 vol. 7 Issue 11 (8 pages).
"International Application Serial No. PCT US2019 013799, Written Opinion dated Apr. 12, 2019", 8 pgs.
"International Application Serial No. PCT US2019 013799, International Search Report dated Apr. 12, 2019", 4 pgs.
Bolandzadeh, N, "Multimodal Registration of Three-Dimensional Maxillodental Cone Beam CT and Photogrammetry Data Over Time", Dento-Maxillo-Facial Radiology, vol. 42, No. 2., (Feb. 1, 2013), 9 pgs.
Hamadeh, Ali, "Anatomy-based Registration for Computer-Integrated Surgery.", First International Conference, CVR Med. '95 Nice, France, Joint Conference Computer Vision, Virtual Reality and Roboticsin Medicine and Medical Robotics and Computer-Assisted Surgery Proceedings, (Apr. 3, 1995), 212-218.
Stefania, Pallotta, "Accuracy of a 3d Laser Camera Surface Imaging System for Setup Verification of the Pelvic and Thoracic Regions in Radiotherapy Treatments", Medical Physics, AIP, Melville, NY, US, vol. 40, No. 1., (Jan. 1, 2013), 8 pgs.
Youngjun, Kim, "Accuracy of surface registration compared to conventional volumetric registration in patient positioning for head-and-neck radiotherapy: A simulation study using patient data", Medical Physics, AIP, Melville, NY, US, vol. 41, No. 12, (Dec. 1, 2014), 7 pgs.

\* cited by examiner

METHODS AND DEVICES FOR SURFACE MOTION TRACKING

TECHNICAL FIELD

Aspects of the present disclosure relate generally to radiotherapy treatment systems, and, specifically, to methods and systems for merging images of a surface region and an interior region of the body.

BACKGROUND

Radiation therapy (also referred to as radiotherapy) may be used in the treatment of cancer or other pathologies. Radiotherapy involves delivering a prescribed dose of radiation to a target region of a patient, for example, to a tumor or other cancerous tissue. The target region may be imaged prior to the administration of radiotherapy, and a treatment plan may be formulated based on, e.g., the size, location, and/or orientation of the target and the surrounding structures, among other things. A linear accelerator (linac) or other suitable radiation delivery device may then be used to deliver radiation to the target region of the patient. The linac may direct photons (e.g., X-rays), electrons, or other subatomic particles toward a target, such as a tumor.

After initial images of the target are acquired, the location and/or orientation of the target region may change. For example, the patient may shift during transfer to the treatment room, during movement within the treatment room (e.g., positioning on a couch, bed, or table), or during the administration of radiotherapy. For example, a patient may have voluntarily or involuntarily movements due to regular biological processes, including, e.g., breathing, swallowing, blinking, twitching, peristalsis, digestion, beating of the heart, coughing, passing gas, or other movements.

Additionally, tracking anatomy across different radiation therapy treatment sessions (called fractions) may be complicated, because a patient may lose or gain weight between each fraction, a target region (e.g., tumor) may change size (e.g., shrink or get larger), or the anatomy around the target region may affect the position of the target region (e.g., the volume of a patient's bladder may change across fractions, affecting the location of surrounding structures).

Changes in the location and/or orientation of the target region may reduce the efficacy of radiotherapy. For example, if the actual orientation or location of the target region is different than the assumed orientation or location based on prior imaging and/or inaccurate alignment with prior imaging, then the correct dose of radiation may not be delivered to the intended target region. Additionally, surrounding healthy structures may receive radiation instead of, or in addition to, the intended target region. Exposing the wrong area to radiation may ultimately harm or kill surrounding healthy cells. Further, it may be desirable to match images of the patient's anatomical structures taken across fractions and/or to an original CT image taken of the patient to track the location of dose delivery and the overall dose delivered to the patient.

Accurate image alignment and tracking techniques may be desirable for radiotherapy to account for movement of anatomy (e.g., movement of a tumor or movement of surrounding healthy structures) and changes in anatomy (e.g., changes in tumor size or weight gains or losses) over the course of treatment (e.g., planning, prepping across fractions) and as radiation is delivered to the patient during a fraction. It may also be desirable to track the location of dose delivery and the overall dose delivered. Accordingly, a need exists for systems and methods that improve the ability to align and compare images of a patient taken at different points in time.

SUMMARY OF THE DISCLOSURE

Embodiments of the disclosure may be directed to an image processing system configured to receive a medical image of a region of a subject's body taken at a first time and to receive a surface image of an exterior portion of the region of the subject's body taken at the first time. The image processing may also be configured to receive a medical image of the region of the subject's body taken at a second time and to register the medical image taken at the first time, the surface image taken at the first time, and the medical image taken at the second time.

Various embodiments of the system may include one or more of the following features: registering the medical image may include using deformable registration; the second time may precede the first time; the medical image taken at the second time may be a planning computed tomography image; the medical image taken at the first time may either be a magnetic resonance image or a cone-beam computed tomography image; the system may be further configured to obtain the medical image at the first time and obtain the surface image at the first time; the surface image may be one of an optical image, an infrared image, a thermal image, or a stereoscopic image; the medical image taken at the first time, the surface image taken at the first time, and the medical image taken at the second time may be registered simultaneously; the register step may include registering the medical image taken at the first time and the surface image taken at the first time to form a combined image, and then registering the combined image with the medical image taken at the second time; and the medical image taken at the second time may include at least part of the exterior portion of the region of the subject's body.

Embodiments of the disclosure may also be directed to a computer-implemented image processing method. The method may comprise receiving a first medical image of a region of a subject's body taken at a first time, receiving a first surface image of an exterior portion of the region of the subject's body at the first time, and registering the first medical image and the first surface image using deformable registration or imaging system(s) calibration to form a first combined image. The method may also comprise receiving a second medical image of the region of the subject's body taken at a second time, receiving a second surface image of the exterior portion of the region of the subject's body at the second time, and registering the second medical image and the second surface image using deformable registration or imaging system(s) calibration to form a second combined image. The method may also comprise registering the first combined image and the second combined image.

Various embodiments of the method may include one or more of the following features: the first medical image and the second medical image may be either magnetic resonance images or cone-beam computed tomography images; the first surface image and the second surface image may be an optical image, an infrared image, a thermal image, or a stereoscopic image; and the first time and the second time may both occur during a single radiotherapy treatment fraction.

Embodiments of the disclosure may also be directed to a non-transitory computer-readable medium storing instructions that, when executed by a processor, cause the processor to perform an image processing method. The method may comprise receiving a medical image of an interior region of a subject's body taken at a first time, receiving a surface image of an exterior portion of the interior region of the subject's body taken at the first time, and receiving a medical image of the interior region of the subject's body taken at a second time. The method may further comprise registering the medical image taken at the first time, the surface image taken at the first time, and the medical image taken at the second time using deformable registration.

Various embodiments of the method may include one or more of the following features: the surface image may be one of an optical image, an infrared image, a thermal image, or a stereoscopic image; the medical image taken at the second time may be a planning computed tomography image, and the medical image taken at the first time may be either a magnetic resonance image or a cone-beam computed tomography image; the planning computed tomography image may also include at least some of the exterior portion of the interior region of the subject's body; the second time may have occurred during a planning stage, and the first time may have occurred during a radiotherapy treatment fraction; and the medical image taken at the first time, the surface image taken at the first time, and the medical image taken at the second time may be registered simultaneously.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings.

DETAILED DESCRIPTION

Figure 1:
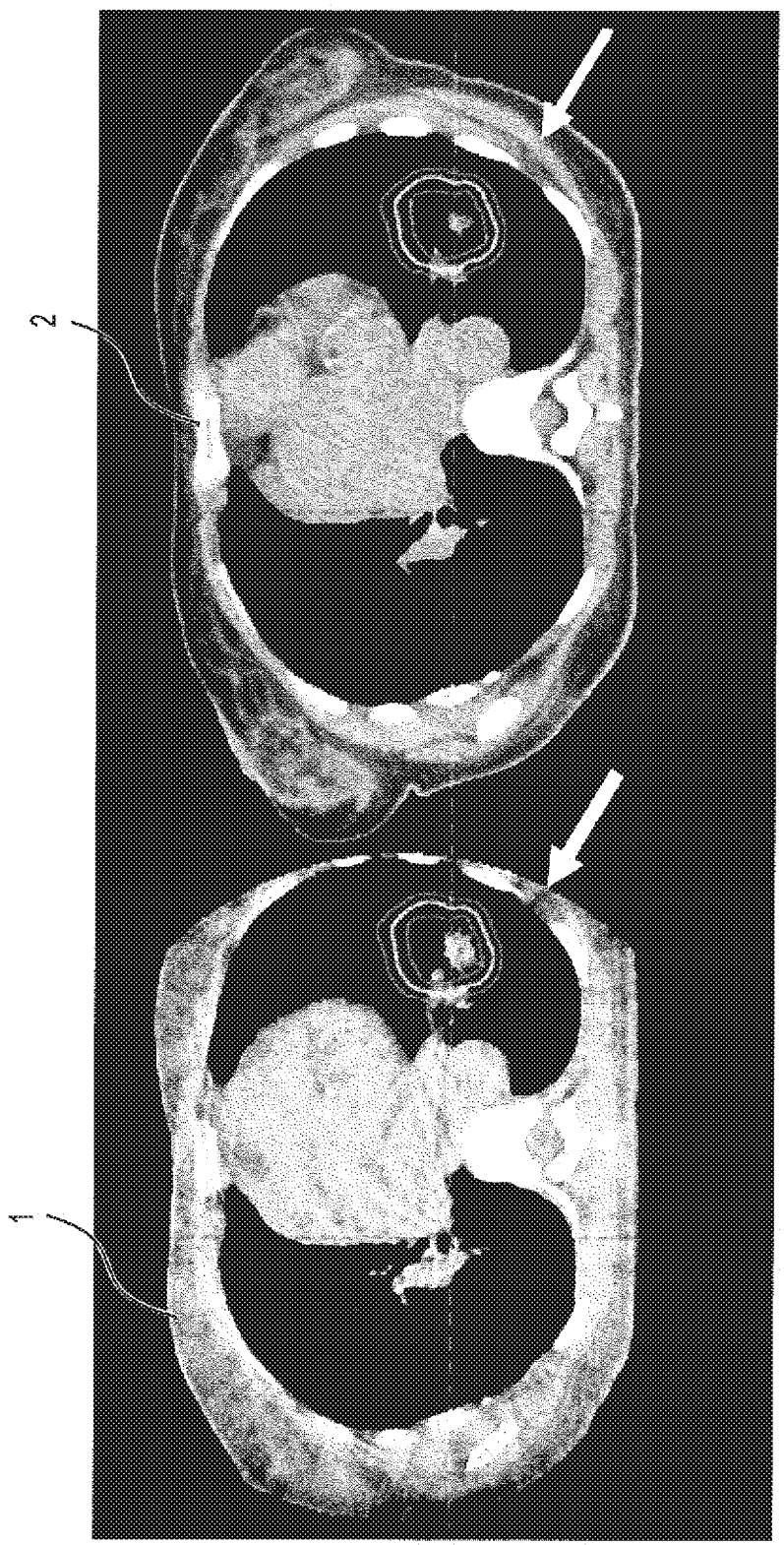
FIG. 1 shows a comparison between a computed tomography image and a cone-beam computed tomography image.

Reference will now be made in detail to the exemplary embodiments of the present disclosure described below and illustrated in the accompanying drawings. Wherever possible, the same reference numbers will be used throughout the drawings to refer to same or like parts. The term "exemplary" is used in the sense of "example," rather than "ideal."

As discussed above, tracking the location of patient anatomy during radiotherapy and/or across treatment fractions of radiotherapy promotes accurate radiation delivery. Tracking anatomy across fractions may be complicated, however, because a patient may lose or gain weight between fractions, a target region (e.g., tumor) may change size (e.g., shrink or get larger), or the anatomy around the target region may affect the position of the target region (e.g., the volume of a patient's bladder may change across fractions, affecting the location of surrounding structures). Yet, it may be desirable to match images of the patient's anatomical structures taken across fractions and/or to an original computed tomography (CT) image taken of the patient to track the location of dose delivery and the overall dose delivered. For example, cone-beam CT (CBCT) images may be taken during treatment and/or while positioning a patient, and these CBCT images may be matched with an original CT image of the patient. It may further be desirable to adapt radiotherapy delivery to accommodate changes in anatomy detected in the images.

For radiotherapy, e.g., adaptive radiotherapy, imaging of a patient is frequently performed in order to track anatomical or functional changes in the patient over the course of treatment, which may include a single treatment session (fraction) or multiple fractions. For example, CBCT or MR imaging may be used for positioning a patient relative to a radiation delivery machine so that radiation is delivered to the intended target area during radiotherapy. Many linear accelerators (linacs) have the ability to generate a 3D CBCT image of the patient at each treatment fraction before and/or during treatment. As another example, a magnetic resonance image linac (MRIL) machine may be able to acquire real-time MR images of the patient during the administration of treatment.

Embodiments of the disclosure may allow for the registration of different images and/or different image types of the same subject for improved alignment and/or tracking by using surface imaging in addition to medical imaging. In exemplary embodiments, surface images may be registered or aligned (e.g., using deformable image registration or through imaging system calibration) with captured medical images (e.g., CT, CBCT, MR, ultrasound, X-ray, positron emission tomography (PET), single-photon emission computed tomography (SPECT) or any other suitable type of medical imaging) to allow for improved alignment and comparison with other medical images. As used herein, "register" and "align" may be used interchangeably to combine data from two different images.

For example, registration of CBCT or MR images may be performed to determine anatomical changes over the course of radiotherapy and/or to evaluate the accumulated radiation dose delivered to the patient. CBCT and/or MR images may be compared with an original CT image taken prior to radiotherapy, e.g., during treatment planning, in order to align and/or track the location of the patient's anatomy before and/or during radiotherapy treatment. The CBCT and/or MR images to be registered may be taken on the day of treatment and may be combined with one or more similar images (e.g., images of a similar region of a subject) from previous treatment days or earlier on the same treatment day, or the CBCT and/or MR images may be registered with a reference CT or MR image, which may have been, for example, taken during treatment planning, or a combination thereof. In embodiments of the present disclosure, these images may also be registered with images of the surface of the patient's body in order to more accurately track the anatomy of the patient, as will be described further below.

Due to time constraints and/or other limitations, during a treatment fraction, CBCT or MR images (commonly referred to as "online" CBCT or MR images) may have a more limited field-of-view of the patient's body compared to a typical CT or MR image used for diagnosis or treatment planning. An online CBCT or MR image often contains only the interior portion of the patient's body. For example, a CBCT image of a region of interest located in a patient's lung may show only the patient's lung and may show no skin or incomplete information about the patient's skin. The anatomy missing from the image, such as the surface of the patient's body (e.g., surface of the skin), may make it difficult to accurately align CBCT and/or MR images to a reference image or to one or more similar (e.g., taken of a similar body region), previously acquired images. For example, the surface of the skin may define the exterior boundary of the patient's body. Without being able to visualize the skin surface, it may not be clear where the patient's body ends, making it harder to align images, determine the path of radiotherapy, determine dosing, and the like.

CBCT and MR images may show mostly or only the interior anatomy of a region of interest, but a full body image may be needed to calculate the dose of radiotherapy delivered to a patient. For example, if a patient loses weight, the location of the skin may change, and the skin surface defines the exterior range of the patient's body. Without knowing the location of the skin surface, it may not be possible to know the location and/or positioning of the body of the patient or the full path of the delivered radiation through the body. As another example, if a patient's bladder is full during a first treatment fraction and not as full during another treatment fraction, organs or structures around the bladder may be located in slightly different places in imaging from the two different fractions. Again, without knowing the location of the skin surface of the patient, it may be difficult to properly align the two medical images.

Although some CBCT images provide a clear skin surface boundary, many CBCT images may cut off or delete areas of the patient's body so that portions of the patient's body are missing from the captured CBCT image. This may occur, for example, due to the size of the patient (e.g., the patient's anatomy may be too large to entirely capture in the image field), or the field of view of the image may be intentionally decreased by the healthcare provider to reduce scatter and/or enhance the quality of the image. For example, FIG. 1 depicts a CT image 2 on the right and a CBCT image 1 on the left. While the CT image shows a defined surface (e.g., skin) of the patient, portions of the surface of the patient in the CBCT image are either cut off or are unclear.

Yet combining images of the external surface of the patient's body (e.g., the patient's skin) with images of internal anatomy captured using the CBCT (e.g., utilizing deformable registration or system calibration) may allow for more complete image information regarding the patient's position and/or movement and thus for better organ tracking by allowing the skin to be tracked. To combine CBCT images of the interior anatomy with the images of the external surface of the patient's body, the two images may be aligned with one another via system calibration or registered with one another. The images of the surface of the patient's body may drive the process of deformable registration with subsequent images, and alignment or registration of the surface image with the interior organ image may be used where the exterior surface is missing either in whole or in part from the CBCT image. With the missing CBCT image information provided via registration with the surface imaging, the combined image may then be registered with a second medical image of the same patient, e.g., a planning CT image.

In MR images, the surface of a patient's skin may include geometric distortion inaccuracies compared to the surface of the patient's skin as captured in a CT image, e.g., a CT image from treatment planning. MR images may not provide a defined surface boundary, and the edges of an MR image may be blurred, making the edges fuzzy and therefore making it difficult to define the skin's outer surface boundary. However, combining the MR images with one or more images of the external surface of the patient's body taken using 3D cameras may decrease or remove the MR distortion. Removing the distortion may improve the registration of the MR image to other images (e.g., CT or ultrasound) by utilizing the skin surface as a constraint to drive image registration. Additionally, as with CBCT images, MR images may be missing information regarding the exterior surface of the body. It is possible that there may be missing information in both MR images and CBCT images.

As a result of this missing and/or inaccurate skin surface information, registration of MR or CBCT images with CT images may be incorrect, and mathematical interpolation may be needed to attempt to account for these inaccuracies. Embodiments of the present disclosure, however, provide an alternative solution. By using a surface imaging system to capture surface images of a patient, missing information from MR and/or CBCT images may be accounted for, and more precise image registration may be possible. The body surface image data combined with the medical image (e.g., CBCT/MR image) data may result in more accurate alignment of the patient anatomy to a planning CT or MR image, or to similar images acquired on the same day or on a previous treatment day. The body surface imaging may be used as complementary data to a CBCT and/or an MR image, and the combined data may be used to guide image registration of the CBCT or MR to another set of 3D data with (in the case of CBCT/MR) or without (in the case of CT) its own surface imagery data.

In embodiments of the disclosure, surface imaging may be combined with a first medical image, and the combined data may be used to guide image registration of the first medical image with a second medical image with or without its own surface imaging data. Surface-tracking images of the skin may be acquired using three-dimensional (3D) and/or two-dimensional (2D) cameras positioned external to the patient, allowing the surface of the patient's skin to be imaged and/or tracked. With the help of surface imaging technologies, such as one or more cameras, one or more real-time images of the exterior surface of the patient body may be acquired while medical images of an interior region (e.g., CBCT, CT, and/or MR images) are being acquired. By acquiring surface images, as well as CBCT, CT, and/or MR images at the same time, the location of the outer boundary of the patient's body may be known at the time the medical images were taken, and the surface imaging may provide a constraint to guide the registration of one or more CBCT, CT, and/or MR images. Rather than trying to align a CBCT image with a CT image, for example, the surface imaging may be used in addition in order to guide the registration by providing a known surface boundary for aligning the images. Although CBCT, CT, and MR imaging is discussed in the above examples, it is contemplated that embodiments of the present disclosure may be drawn to using surface imaging of a patient to align one or more medical images of any suitable type, for example, CT, CBCT, MR, ultrasound, X-ray, PET, SPECT, or any other type of medical imaging.

Any suitable type of cameras, or combinations of cameras, may be used to acquire images of the external surface of a patient. For example, optical, infrared, stereoscopic (e.g., red, green, blue (RGB) stereoscopic), thermal imaging, time-of-flight, and/or structured-light cameras may be used. In some embodiments, Kinect technology, which includes a color video graphics array (e.g., RGB) camera and a depth sensor (including an infrared projector), may be used. A projector may project a pattern into the room, and a camera (e.g., depth sensor) that can read the projected pattern may be used to determine motion, position, and/or depth. In some embodiments, one or more still cameras may be used, while in other embodiments, one or more video cameras may be used, or a combination thereof. Indeed, one or more cameras with any suitable rate of image acquisition may be used.

In some embodiments, two or more external cameras may obtain images of the patient before, during, and/or after radiotherapy. In some embodiments, three cameras may be used, or four or more cameras may be used. The surface imaging cameras may be oriented in the same coordinate system as the radiotherapy delivery device, e.g., the linac or MRIL. For example, the cameras may be mounted to the radiotherapy delivery device so that the surface image data is automatically aligned to the CBCT or MR data, which may allow the recipient of the imaging information to know the location of the center point of the images taken. In some embodiments, one or more cameras may be mounted on other portions of the radiotherapy delivery system, for example, a surface on which the patient is positioned, and/or one or more cameras may be mounted within the treatment area, e.g., on the ceiling, floor, and/or wall of the room. The specific arrangement of one or more cameras relative to each other, relative to the radiotherapy delivery device, and/or relative to the patient, may depend, at least in part, on the type of surface imaging system utilized.

To combine surface imaging with medical imaging (e.g., CT, CBCT, MR, ultrasound, or other imaging), an image of the skin's surface may be registered with a medical image of the internal patient anatomy. A surface camera system (e.g., one or more 2D or 3D cameras) may be used to acquire real-time images of the surface of a patient's body (e.g., the patient's skin) while medical images are being acquired. Because the surface imaging is taken at the same time as the medical imaging, the surface imaging may provide a more accurate definition of the location of the boundaries of the patient's body while the medical imaging was taken. The surface imaging may be combined with the medical imaging taken at that time to provide information about the boundary (e.g., skin surface) of the patient that may be missing from, incomplete, or inaccurate in the internal medical imaging. By providing the accurate surface imaging information to the medical imaging, the combined medical imaging may then be aligned more accurately with a planning CT, MR image, or other medical imaging, which may include partial or complete patient surface information. Accordingly, by combining the surface and medical imaging taken at the same time, more accurate alignment of the patient anatomy to a planning CT, MR image, or to other images acquired at a different time (e.g., earlier on the same treatment day or on a different treatment day) may be achieved. By knowing the location of the boundary of the patient (e.g., the location of the surface of the patient's body) when medical images are taken, it may be easier to align medical images of internal structures of a patient by aligning the boundaries of the patient (e.g., aligning the surface of the skin) across the medical images.

Deformable registration or alignment through, e.g., system calibration may be used to combine a surface image with a medical image to recreate missing information and/or to correct information from the medical image. Images of the surface of the patient's body may be registered or aligned with one or more medical images of an interior region (e.g., of an organ, tumor, or other anatomy) to provide more complete image information and improved tracking of a patient's interior anatomy. The surface imaging may be registered with interior medical imaging where the surface information is missing from the medical imaging either in whole or in part. For example, with smaller fields of view to reduce scatter and enhance the quality of the image, the skin surface may be cut-off, or all of the patient's body may not fit into the field of view. The combined surface image and medical image are referred to herein as a combined image, which may consist of one or more data points and/or full images of the surface and/or interior region of the patient. The surface image may be used as a constraint to drive the subsequent deformable registration to one or more other medical images, such as a planning CT, which may have surface information that is extractable using image segmentation methods.

Registration of two or more images may involve determining an optimization equation for image transformation. One transformation may align a pair of images. The mapping function of transformation may be found in order to associate points between two images. Mathematically, the goal of image registration may be to find an optimal mapping T: $R^3 \rightarrow R^3$ (wherein T represents transformation, and T can be linear or nonlinear) between points of two images (e.g., images I and J) such that given a point x in image I, y=T(x) defines the corresponding point in image J. Finding the optimal T for any given two images I and J may generally be formulated as an optimization problem, e.g.:

$$T_{opt} = \arg\min_T C(T;I,J) + w_1 R(T),$$

where C(T;I,J) measures the misalignment (i.e., "dissimilarity") between the two images under the transformation T, R(T), which measures the irregularity of the transformation T, and $w_1$ denotes a weighting factor that controls the relative importance of the two terms. Some examples of C(T;I,J) include taking the sum-of-squared-differences (SSD), the mutual information (MI), the cross-correlation, or other suitable imaging metrics. The amount of contrast present in a medical image may at least in part depend on the type of imaging used (e.g., MRI, CT, CBCT, etc.). Depending on the type of imaging used, different image metrics may be suitable. For example, in some embodiments, cross-correlation may be used for CBCT images, and in some embodiments, MI may be used for MR images. Imaging metrics may be used to make two images being registered appear more similar to each other to assist with matching the different images. Examples of R(T) include the bending energy, the elastic energy, the gradient magnitude of T, the curvature of T, etc. The above examples are generally drawn to intensity based comparisons of the two images, but it is also contemplated that the images may be registered by feature extraction (e.g., via the use of points or fiducials positioned on a patient's skin), or other suitable methods.

As mentioned earlier, if either the image I or the image J is a CBCT or an online MR image, it may contain only a partial (interior) region of the patient's body. As a result, the optimal transformation T may only be found for the limited region as well. No correspondences may be found for points on the surface (e.g., skin) of the patient. In embodiments of the disclosure using a surface imaging system, however, it may be possible to acquire surface data of the patient. With the surface data available, it may then be possible to obtain a more accurate and more complete estimation of the transformation between the patient anatomies at two different time points through a simultaneous image and surface registration:

$$T_{opt}=\arg \min_T C(T;I,J)+w_1 D(T;S_I,S_J)+w_2 R(T).$$

The term $D(T;S_I,S_J)$ measures the misalignment of two surfaces, one for each of the two images. For example, $D(T;S_I,S_J)$ may be defined as the average distance between corresponding points of the two surfaces. Variables $w_1$ and $w_2$ are two weighting factors. In embodiments of the disclosure, it may be assumed that the surfaces ($S_I$ and/or $S_J$) correspond to the skin surface of the patient. If image I (or J) is a planning CT or MR image that already contains the skin surface of the patient body, it may be possible to extract $S_I$ (or $S_J$) directly from the image through image segmentation methods (either automatic or manual segmentation). If image I (or J) is a CBCT or online MR image that doesn't contain the skin surface of the patient body, it may be possible to then acquire and extract $S_I$ (or $S_J$) from the surface imaging data that were captured at the same time of the CBCT or MR image, using suitable image processing methods.

While some embodiments of the disclosure are directed to combining online CBCT or MR imaging with surface imaging to align the combined image with a planning CT, for example, some embodiments of the disclosure may be used for adaptive radiotherapy treatment. Thus, instead of aligning online CBCT or MR imaging with surface imaging to a planning CT, it may be possible to align a series of CBCT or MRI and surface-imaging pairs for online adaptive or tracking. For example, during treatment (either during the same day or across multiple days), multiple medical images (e.g., multiple CBCT images or multiple MRI images) may be taken of a patient. At the same time, multiple surface images may be taken of the patient's skin surface. Pairs of CBCT images and surface images taken at the same time, or pairs of MRI and surface images taken at the same time, may then be compared to other CBCT/surface or MRI/surface pairings taken at different time points. Because the imaging pairs (pairs of medical and surface images taken at the same time) include surface data, they may be easier to align with one another. Accordingly, it may not matter that one or more of the CBCT or MR images may contain missing or inaccurate information regarding the surface of the patient, because the surface image taken at the same time as the medical image may provide that missing information. In this manner, the image pairs may be used to track movement of the patient during treatment, either intermittently or continuously. In some embodiments, if too much movement is detected, treatment may be stopped and/or altered.

In some embodiments, instead of solving the combined surface and image registration problem, it may be possible to solve the surface and the image alignment problem separately. For example, the medical image and the surface image from a first time may be aligned, e.g., via system calibration, or registered, and then the combined image may be registered to a second medical image from a second time. The final transformation may be obtained by combining the two results. In some aspects, however, the simultaneous optimization of the image and surface registration may lead to more stable and more accurate results.

In addition to providing more accurate alignment of the patient anatomy, embodiments of the disclosure may use the surface imaging data to help correct MR image distortion. For example, the MR image may contain information about the exterior body region, and the skin surface may be extracted from the MR image itself. However, the MR image may suffer from geometric distortion, and the surface extracted from the MR image may not accurately match the true physical surface of the patient. Using surface imaging in accordance with the present disclosure may provide the ability to estimate and correct the MR distortion by finding an optimal (nonlinear) transformation T for the following surface-to-surface matching problem:

$$T_{opt}=\arg \min_T D(T;S_I,S_J)+w_1 R(T),$$

where $S_I$ can be assumed to be the distorted skin surface extracted directly from the MR image, and $S_J$ is the correct skin surface extracted from the surface imager.

Figure 2:
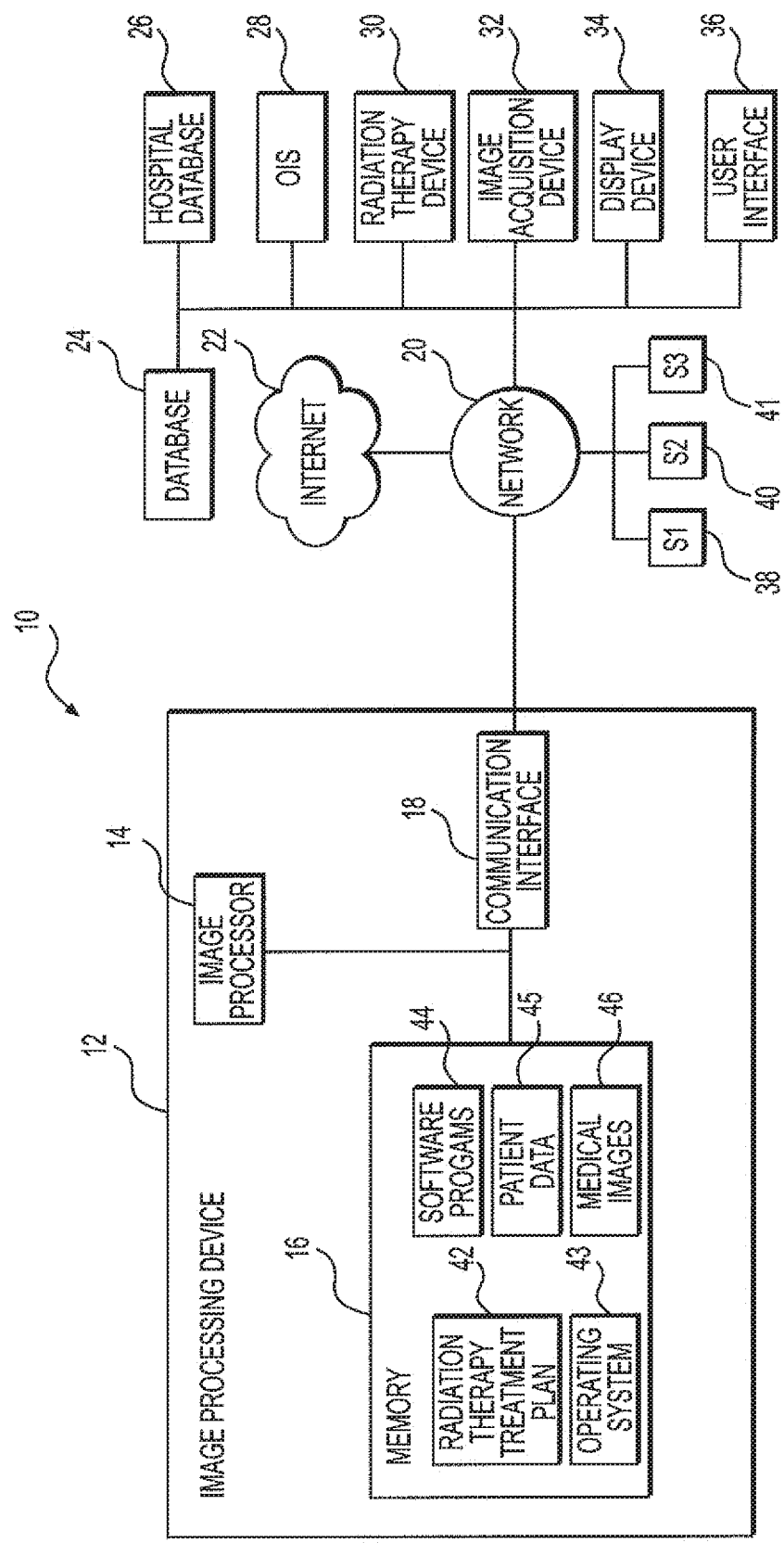
FIG. 2 illustrates an exemplary radiation therapy system, according to embodiments of the present disclosure.

FIG. 2 illustrates an exemplary radiotherapy system 10 for providing radiation therapy to a patient with which embodiments of the disclosure may be used and/or executed. Radiotherapy system 10 includes an image processing device 12. Image processing device 12 may be connected to a network 20. Network 20 may be connected to Internet 22. Network 20 may connect image processing device 12 with one or more of a database 24, a hospital database 26, an oncology information system (01S) 28, a radiation therapy device 30, an image acquisition device 32, a display device 34, and/or a user interface 36. Image processing device 12 may be configured to generate one or more radiation therapy treatment plans 42 to be used by radiation therapy device 30.

Image processing device 12 may include a memory 16, an image processor 14, and/or a communication interface 18. Memory 16 may store computer-executable instructions, such as an operating system 43, one or more radiation therapy treatment plans 42 (e.g., original treatment plans, and/or adapted treatment plans), software programs 44 (e.g., artificial intelligence, deep learning, neural networks, and/or radiotherapy treatment plan software), and/or any other computer-executable instructions to be executed by image processor 14. In some embodiments, software programs 44 may convert medical images of one format (e.g., MRI) to another format (e.g., CT) by producing synthetic images, such as a pseudo-CT image. For instance, software programs 44 may include image processing programs to train a predictive model for converting a medial image 46 in one modality (e.g., an MRI image) into a synthetic image of a different modality (e.g., a pseudo CT image); alternatively, the trained predictive model may convert a CT image into an MRI image. In some embodiments, software programs 44 may register one or more medical images and one or more surface images, as discussed in the embodiments herein. Memory 16 may store data, including medical images 46, surface images, patient data 45, and/or other data required to create and/or implement radiation therapy treatment plan 42.

In addition to, or instead of, memory 16 storing software programs 44, it is contemplated that software programs 44 may be stored on a removable computer medium, such as a hard drive, a computer disk, a CD-ROM, a DVD, an HD, a Blu-Ray DVD, a USB flash drive, an SD card, a memory stick, or any other suitable medium. Software programs 44, when downloaded to image processor 14, may be executed by image processor 14.

Image processor 14 may be communicatively coupled to memory 16, and image processor 14 may be configured to execute computer-executable instructions stored thereon. Image processor 14 may send or receive medical images 46, or surface images, to memory 16. For example, image processor 14 may receive medical images 46, or surface images, from image acquisition device 32, or another image acquisition device, via communication interface 18 and network 18 to be stored in memory 16. Image processor 14 may also send medical images 46, or surface images, stored in memory 16 via communication interface 18 to network 20 be stored in database 24 and/or hospital database 26.

Further, image processor 14 may utilize software programs 44 (e.g., a treatment planning software) along with medical images 46, surface images, and/or patient data 45 to create and/or modify radiation therapy treatment plan 42. Medical images 46 may include information such as imaging data associated with a patient anatomical region, organ, or volume of interest segmentation data. Patient data 45 may include information such as (1) functional organ modeling data (e.g., serial versus parallel organs, appropriate dose response models, etc.); (2) radiation dosage data (e.g., dose-volume histogram (DVH) information); and/or (3) other clinical information about the patient and course of treatment (e.g., other surgeries, chemotherapy, previous radiotherapy, etc.). Surface images may include any suitable imaging type capturing information about an external surface of the patient (e.g., the patient's skin surrounding a region of interest).

In addition, image processor 14 may utilize software programs to generate intermediate data, such as updated parameters to be used, for example, by a neural network model, or to generate an intermediate 2D or 3D image, which may then subsequently be stored in memory 16. Image processor 14 may then transmit executable radiation therapy treatment plan 42 via communication interface 18 to network 20 to radiation therapy device 30, which may execute radiation therapy treatment plan 42 to treat a patient with radiation. In addition, image processor 14 may execute software programs 44 to implement functions, such as, e.g., image conversion, image segmentation, deep learning, neural networks, and/or artificial intelligence. For instance, image processor 14 may execute software programs 44 that train and/or contour a medical image. Such software programs 44, when executed, may train a boundary detector and/or utilize a shape dictionary.

Image processor 14 may be a processing device, include one or more general-purpose processing devices such as a microprocessor, a central processing unit (CPU), a graphics processing unit (GPU), and/or an accelerated processing unit (APU), for example. More particularly, in some embodiments, image processor 14 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. Image processor 14 may also be implemented by one or more special-purpose processing devices, such as an application specific integrated circuit (ASIC), a field programmable gate array (FPGA), a digital signal processor (DSP), a System on a Chip (SoC), or other suitable processors. As would be appreciated by those skilled in the art, in some embodiments, image processor 14 may be a special-purpose processor, rather than a general-purpose processor. Image processor 14 may include one or more known processing devices, such as a microprocessor from the Pentium™, Core™ Xeon™, or Itanium® family manufactured by Intel™ the Turion™ Athlon™ Sempron™ Opteron™ FX™, Phenom™ family manufactured by AMD™, or any of various processors manufactured by Sun Microsystems. Image processor 14 may also include graphical processing units, such as a GPU from the GeForce®, Quadro®, Tesla® family manufactured by Nvidia™ GMA, Iris™ family manufactured by Intel™, or the Radeon™ family manufactured by AMD™. Image processor 14 may also include accelerated processing units, such as the Desktop A-4(6,8) Series manufactured by AMD™, or the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein.

In addition, the term "processor" may include more than one processor, for example, a multi-core design, or a plurality of processors each having a multi-core design. Image processor 14 may be configured to execute sequences of computer program instructions, e.g., those stored in memory 16, to perform various operations, processes, and methods according to exemplary embodiments of the disclosure.

Memory 16 may store medical images 46 and/or surface images. In some embodiments, medical images 46 may include, e.g., one or more MR image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), CT image (e.g., 2D CT, CBCT, 3D CT, 4D CT), ultrasound image (e.g., 2D ultrasound, 3D ultrasound, 4D ultrasound), PET image, X-ray image, fluoroscopic image, radiotherapy portal image, SPECT image, and/or computer-generated synthetic image (e.g., pseudo-CT images). Further, medical images 46 may include medical image data, for example, training images, ground truth images, and/or contoured images. Images stored in memory 16 may include registered and/or unregistered images, and the images may have been pre-processed or may be raw, unprocessed images. In some embodiments, medical images 46 may be received from image acquisition device 32. Accordingly, image acquisition device 32 may include an MR imaging device, a CT imaging device, a PET imaging device, an ultrasound imaging device, a fluoroscopic device, a SPECT imaging device, an integrated linac and MR imaging device, or other medical imaging devices for obtaining the medical images of the patient. Medical images 46 may be received and stored in any type of data or any type of format that image processing device 12 may use to perform operations consistent with the disclosed embodiments.

Memory 16 may be a non-transitory computer-readable medium, such as a read-only memory (ROM), a phase-change random access memory (PRAM), a static random access memory (SRAM), a flash memory, a random access memory (RAM), a dynamic random access memory (DRAM), such as synchronous DRAM (SDRAM), an electrically erasable programmable read-only memory (EEPROM), a static memory (e.g., flash memory, flash disk, static random access memory) or any other suitable type of random access memory, e.g., a cache, a register, a compact disc read-only memory (CD-ROM), a digital versatile disc (DVD) or other optical storage, a cassette tape, other magnetic storage device, or any other non-transitory medium that may be used to store information including images, data, or computer executable instructions (e.g., stored in any format) capable of being accessed by image processor 14, or any other type of computer device. The computer program instructions may be accessed by image processor 14, read from the ROM, or any other suitable memory location, and loaded into the RAM for execution by image processor 14. For example, memory 16 may store one or more software applications. Software applications stored in memory 16 may include, for example, an operating system 43 for common computer systems, as well as for software-controlled devices. Further, memory 16 may store an entire software application, or only a part of a software application, that may be executable by image processor 14. For example, memory 16 may store one or more radiation therapy treatment plans 42.

Image processing device 12 may communicate with network 20 via communication interface 18, which may be communicatively coupled to image processor 14 and memory 16. Communication interface 18 may provide communication connections between image processing device 12 and radiotherapy system 10 components (e.g., permitting the exchange of data with external devices). For example, communication interface 18 may, in some embodiments, have appropriate interfacing circuitry to connect to user interface 36, which may be, e.g., a hardware keyboard, a keypad, and/or a touch screen through which a user may input information into radiotherapy system 10.

Communication interface 18 may include, for example, one or more of a network adaptor, a cable connector, a serial connector, a USB connector, a parallel connector, a high-speed data transmission adaptor (e.g., fiber, USB 3.0, thunderbolt), a wireless network adaptor (e.g., WiFi adaptor), a telecommunication adaptor (e.g., 3G, 4G/LTE), or other suitable interfaces. Communication interface 18 may include one or more digital and/or analog communication devices that may permit image processing device 12 to communicate with other machines and devices, such as remotely located components, via network 20.

Network 20 may provide the functionality of, for example, a local area network (LAN), a wireless network, a cloud computing environment (e.g., software as a service, platform as a service, infrastructure as a service, etc.), a client-server, or a wide area network (WAN). For example, network 20 may be a LAN or a WAN that may include other systems S1 (38), S2 (40), and S3 (41). Systems S1, S2, and S3 may be identical to image processing device 12 or may be different systems. In some embodiments, one or more systems in network 20 may form a distributed computing/simulation environment that may collaboratively perform the embodiments described herein. In some embodiments, one or more systems S1, S2, and S3 may include a CT scanner that obtains CT images (e.g., medical images 46). In addition, network 20 may be connected to Internet 22 to communicate with servers and clients that reside remotely on the Internet.

Therefore, network 20 may allow data transmission between image processing device 12 and a number of various other systems and devices, such as OIS 28, radiation therapy device 30, and/or image acquisition device 32. Further, data generated by the OIS 28 and/or image acquisition device 32 may be stored in memory 16, database 24, and/or hospital database 26. The data may be transmitted/received via network 20, through communication interface 18, in order to be accessed by image processor 14, as required.

Image processing device 12 may communicate with database 24 through network 20 to send/receive a plurality of various types of data stored on database 24. For example, database 24 may include machine data that comprises information associated with radiation therapy device 30, image acquisition device 32, and/or other machines and/or devices relevant to radiotherapy. Machine data information may include radiation beam size, arc placement, beam on and off time duration, control points, segments, multi-leaf collimator (MLC) configuration, gantry speed, MRI pulse sequence, and/or other suitable information. Database 24 may be a storage device. One skilled in the art would appreciate that database 24 may include a plurality of devices located either in a central or a distributed manner.

In some embodiments, database 24 may include a processor-readable storage medium (not shown). While the processor-readable storage medium in some embodiments may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing and/or encoding a set of instructions for execution by a processor and that cause the processor to perform any one or more of the methodologies of the present disclosure. The term "processor-readable storage medium" shall accordingly be taken to include, but not be limited to, solid-state memories, optical, and magnetic media. For example, the processor-readable storage medium may be one or more volatile, non-transitory, or non-volatile tangible computer-readable media.

Image processor 14 may communicate with database 24 to read images into memory 16 and/or store images from memory 16 to database 24. For example, database 24 may be configured to store a plurality of images (e.g., 3D MRI, 4D MRI, 2D MRI slice images, CT images, 2D fluoroscopy images, X-ray images, raw data from MR scans or CT scans, Digital Imaging and Communications in Medicine (DIMCOM) data, etc.) that database 24 received from image acquisition device 32 or other image acquisition device. Database 24 may store data to be used by image processor 14 when executing software program 44, and/or when creating radiation therapy treatment plans 42. Image processing device 12 may receive medical images 46 (e.g., 2D MRI slice images, CT images, 2D fluoroscopy images, X-ray images, 3DMR images, 4D MR images, etc.) either from database 24, radiation therapy device 30 (e.g., a MRI-linac), and/or image acquisition device 32 to generate a treatment plan 42.

In an exemplary embodiment, radiotherapy system 100 may include an image acquisition device 32 configured to acquire medical images (e.g., MR images, such as 3D MRI, 2D streaming MRI, or 4D volumetric MRI, CT images, CBCT, PET images, functional MR images (e.g., fMRI, DCE-MRI, and diffusion MRI), X-ray images, fluoroscopic images, ultrasound images, radiotherapy portal images, SPECT images, etc.) of the patient. Image acquisition device 32 may, for example, be an MR imaging device, a CT imaging device, a PET imaging device, an ultrasound device, a fluoroscopic device, a SPECT imaging device, or any other suitable medical imaging device for obtaining one or more medical images of the patient. Images acquired by imaging acquisition device 32 may be stored within database 24 as either imaging data and/or test data. By way of example, the images acquired by imaging acquisition device 32 may be also stored by image processing device 12, as medical image data 46 in memory 16.

Radiotherapy system 100 may also include one or more surface imaging systems, as described above, which may be separate from or incorporated within imaging acquisition device 32. Images acquired by the surface imaging system may be stored within database 24 as either imaging data and/or test data. By way of example, the images acquired by the surface imaging system may be also stored by image processing device 12, as surface imaging data in memory 16.

In some embodiments, for example, image acquisition device 32 may be integrated with radiation therapy device 30 as a single apparatus (e.g., an MRI device combined with a linac, also referred to as an "MRI-Linac." Such an MRI-Linac may be used, for example, to determine a location of a target organ or a target tumor in the patient, so as to direct radiation therapy accurately according to radiation therapy treatment plan 42 to a predetermined target.

Image acquisition device 32 may be configured to acquire one or more images of the patient's anatomy at a region of interest (e.g., a target organ, a target tumor, or both). Each image, typically a 2D image or slice, may include one or more parameters (e.g., a 2D slice thickness, an orientation, a location, etc.). In some embodiments, image acquisition device 32 may acquire a 2D slice in any orientation. For example, an orientation of the 2D slice may include a sagittal orientation, a coronal orientation, or an axial orientation. Image processor 14 may adjust one or more parameters, such as the thickness and/or orientation of the 2D slice, to include the target organ and/or target tumor. In an exemplary embodiment, 2D slices may be determined from information, such as a 3D MRI volume. Such 2D slices may be acquired by image acquisition device 32 in "real-time" while a patient is undergoing radiation therapy treatment, for example, when using radiation therapy device 30. "Real-time" may mean acquiring the data within milliseconds (e.g., 500 milliseconds or 300 milliseconds) or less.

Image processing device 12 may generate and store radiation therapy treatment plans 42 for one or more patients. Radiation therapy treatment plans 42 may provide information about a particular radiation dose to be applied to each patient. Radiation therapy treatment plans 42 may also include other radiotherapy information, such as beam angles, dose-histogram-volume information, the number of radiation beams to be used during therapy, the dose per beam, or other suitable information or combination thereof.

Image processor 14 may generate radiation therapy treatment plans 42 by using software programs 44, for example, treatment planning software, such as Monaco®, manufactured by Elekta AB of Stockholm, Sweden. In order to generate radiation therapy treatment plans 42, image processor 14 may communicate with image acquisition device 32 (e.g., a CT device, an MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, treatment planning device 110 may study the dose distribution not only in the target, but also in the OAR.

In order to delineate a target organ or a target tumor from the OAR, medical images, such as MR images, CT images, PET images, fMR images, X-ray images, ultrasound images, radiotherapy portal images, SPECT images, or other medical images, of the patient undergoing radiotherapy may be obtained by image acquisition device 32 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receive as low a radiation dose as possible). Other parameters that may be considered include the location of the target organ and the target tumor, the location of the OAR, and/or the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by an OAR proximate to the tumor (e.g., left and right parotid, optic nerves, eyes, lens, inner ears, spinal cord, brain stem, or other anatomy). After the radiation dose is determined for relevant anatomical structures (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and/or beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45Gy, ≤55Gy and <54Gy, respectively). The result of inverse planning may constitute a radiation therapy treatment plan 42 that may be stored in memory 16 or database 24. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, image processing device 12 may generate a tailored radiation therapy treatment plan 42 having these parameters in order for radiation therapy device 30 to provide radiotherapy treatment to the patient.

In addition, radiotherapy system 10 may include a display device 34 and a user interface 36. Display device 34 may include one or more display screens configured to display medical images, interface information, treatment planning parameters (e.g., contours, dosages, beam angles, etc.) treatment plans, a target, localizing a target and/or tracking a target, or any suitable information to the user. User interface 36 may be a keyboard, a keypad, a touch screen, or any type of device that a user may input information to radiotherapy system 10. Alternatively, display device 34 and user interface 36 may be integrated into a device such as a smart phone, computer, or tablet computer, e.g., Apple iPad®, Lenovo Thinkpad®, Samsung Galaxy®, etc.

Furthermore, any and all components of radiotherapy system 10 may be implemented as a virtual machine (e.g., VMWare, Hyper-V, etc.). For example, a virtual machine may be software that functions as hardware. Therefore, a virtual machine may include at least one or more virtual processors, one or more virtual memories, and/or one or more virtual communication interfaces that together function as hardware. For example, image processing device 12, OIS 28, and/or image acquisition device 32 may be implemented as a virtual machine. Given the processing power, memory, and computational capability available, the entire radiotherapy system 10 may be implemented as a virtual machine.

Figure 3:
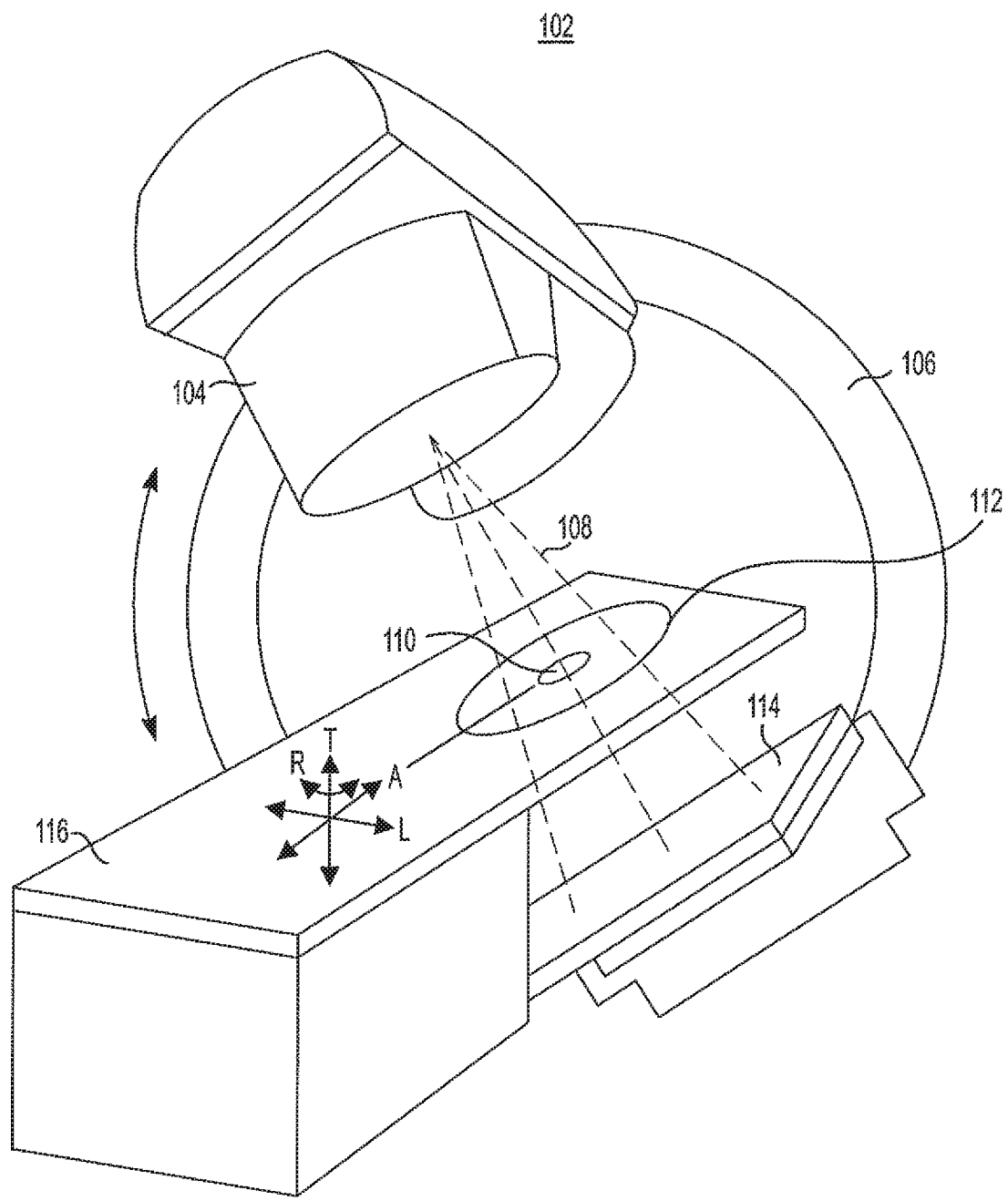
FIG. 3 illustrates an exemplary radiation therapy system, including a radiation therapy output configured to deliver a radiation therapy beam.

FIG. 3 illustrates an exemplary radiation therapy device 102, which may include a radiation source, such as an X-ray source or a linac, a multi-leaf collimator (not shown), a couch 116, an imaging detector 114, and a radiation therapy output 104. Radiation therapy device 102 may be configured to emit a radiation beam 108 to provide therapy to a patient. Radiation therapy output 104 may include one or more attenuators or collimators, such as a multi-leaf collimator (MLC).

Referring back to FIG. 3, a patient may be positioned in a region 112, using a table or couch 116, to receive a radiation therapy dose according to a radiation therapy treatment plan. Radiation therapy output 104 may be mounted or attached to a gantry 106 or other mechanical support. One or more chassis motors (not shown) may rotate gantry 106 and radiation therapy output 104 around couch 116 when couch 116 is inserted into the treatment area. In an embodiment, gantry 106 may be continuously rotatable around couch 116 when couch 116 is inserted into the treatment area. In another embodiment, gantry 106 may rotate to a predetermined position when couch 116 is inserted into the treatment area. For example, gantry 106 may be configured to rotate radiation therapy output 104 around an axis ("A"). Both couch 116 and radiation therapy output 104 may be independently moveable to other positions around the patient, such as moveable in a transverse direction ("T"), moveable in a lateral direction ("L"), or as rotation about one or more other axes, such as rotation about a transverse axis (indicated as "R"). A controller (not shown) communicatively connected to one or more components of radiation therapy device 102 may control movement and/or rotation of couch 116 in order to properly position the patient in or out of radiation beam 108 according to a radiation therapy treatment plan. If both couch 116 and gantry 106 are independently moveable from one another in multiple degrees of freedom, this may allow the patient to be positioned such that radiation beam 108 can precisely target the tumor.

The coordinate system (including axes A, T, and L) shown in FIG. 3 may have an origin located at an isocenter 110. Isocenter 110 may be defined as a location where radiation therapy beam 108 intersects the origin of a coordinate axis, such as to deliver a prescribed radiation dose to a location on or within a patient. For example, isocenter 110 may be defined as a location where radiation therapy beam 108 intersects the patient from various rotational positions of radiation therapy output 104 as positioned by gantry 106 around the axis A.

Gantry 106 may also have an attached imaging detector 114. Imaging detector 114 may be located opposite of radiation source 104, and in some embodiments, imaging detector 114 may be located within a field of therapy beam 108.

Imaging detector 114 may be mounted on gantry 106 opposite radiation therapy output 104, so as to maintain alignment with radiation therapy beam 108. Imaging detector 114 may rotate about the rotational axis as gantry 106 rotates. In some embodiments, imaging detector 114 may be a flat panel detector (e.g., a direct detector or a scintillator detector). In this manner, imaging detector 114 may be used to monitor radiation therapy beam 108, and/or imaging detector 114 may be used for imaging the patient's anatomy, such as via portal imaging. The control circuitry of radiation therapy device 102 may be integrated within system 10 or may be remote from it.

In an illustrative embodiment, one or more of couch 116, radiation therapy output 104, and/or gantry 106 may be automatically positioned, and radiation therapy output 104 may establish radiation therapy beam 108 according to a specified dose for a particular therapy delivery instance. A sequence of therapy deliveries may be specified according to a radiation therapy treatment plan, such as using one or more different orientations or locations of gantry 106, couch 116, and/or therapy output 104. The therapy deliveries may occur sequentially, but may intersect in a desired therapy locus on or within the patient, such as at isocenter 110. A prescribed cumulative dose of radiation therapy may thereby be delivered to the therapy locus while damage to tissue nearby the therapy locus may be reduced or avoided.

Figure 4A:
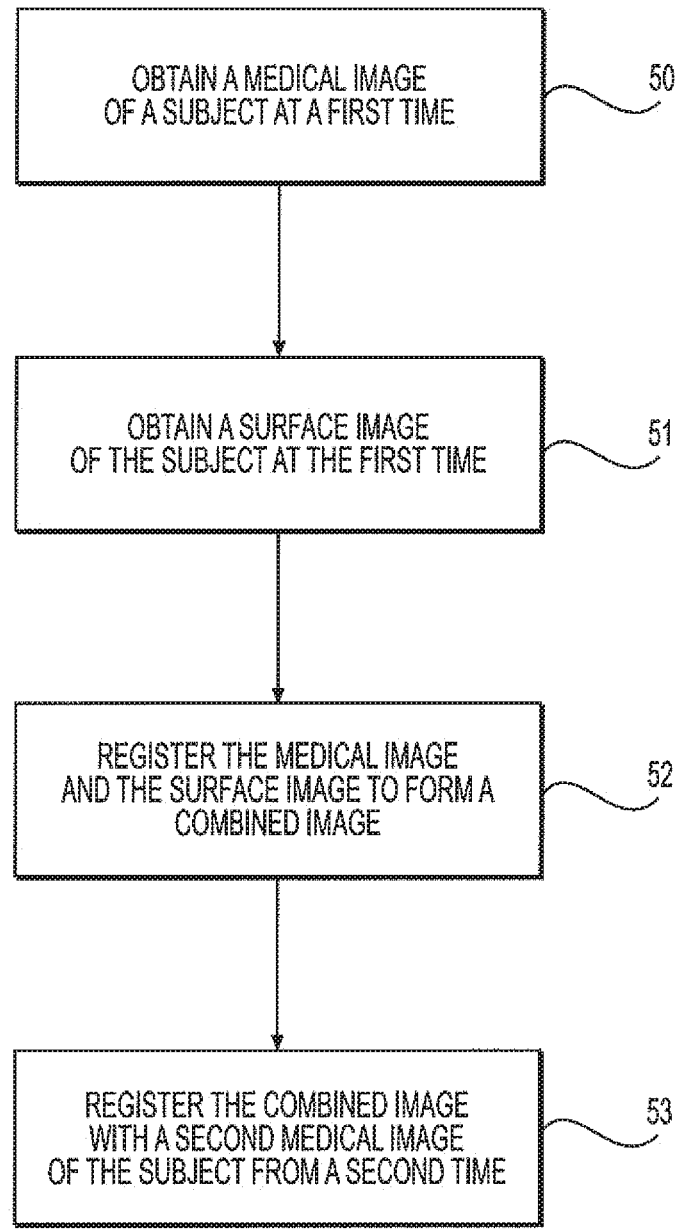
FIG. 4A is a flow chart portraying an exemplary imaging method, according to various embodiments of the present disclosure.

Exemplary methods of the disclosure may be performed in the manner shown in FIG. 4A. First, a medical image of a subject may be obtained at a first time, as shown in step 50. The medical image may include one or more of a CT, CBCT, MR, ultrasound, X-ray, PET, or SPECT image, or any other suitable type of medical imaging. The medical image may be taken by an image acquisition system incorporated into a radiation delivery device, or may be taken by an image acquisition system that is separate from a radiation delivery device. The medical image may be a 2D or a 3D image, for example. The first time may be prior to, during, or after a radiotherapy treatment fraction, or may have occurred during a prior fraction or during treatment planning or patient preparation. Also at the first time, a surface image of the subject may be obtained (step 51), for example, using a surface imaging camera system, which may include one or more cameras. The surface image may be a 2D or a 3D image, for example. The surface imaging camera system may be separate from a radiation delivery device or may be incorporated into a radiation delivery device.

Once the medical image and the surface image are obtained, the medical image and the surface image may be aligned with one another, e.g., via system registration, or registered with each other to form a combined image, step 52. In some embodiments, deformable registration may be used to register the surface image and the medical image. The combined image may include one or more data points or other non-image information to indicate the position of the surface image and/or medical image in the combined image. Registration may be performed using any suitable image processing technology, which may be uploaded and/or stored on any suitable processor, as described further below. The combined image may then be registered with a second medical image of the subject from a second time, step 53, e.g., using deformable registration. The second time may be different than the first time. In some embodiments, the first time may be before, during, or after the delivery of radiotherapy during a treatment fraction, and the second time may be a previous treatment fraction, a later treatment fraction, or a treatment planning or patient preparation stage. It is also possible that the second time may be a different time during the same treatment fraction. It is also noted that the first time does not need to come before the second time; indeed, the second time may precede the first time. The terms 'first' and 'second' simply denote two, separate times.

In some embodiments, the medical image obtained at the first time may be a CBCT or MR image obtained during a treatment fraction, e.g., before, during, or after the delivery of radiotherapy during that fraction. The surface image may be a 3D or 2D image and may be taken with an optical, infrared, stereoscopic (e.g., RGB stereoscopic), time-of-flight, or structured-light surface imaging system, or may be taken using Kinect technology, as described above. The second medical image may be a CT or MR image taken, for example, during a planning or treatment preparation stage.

Figure 4B:
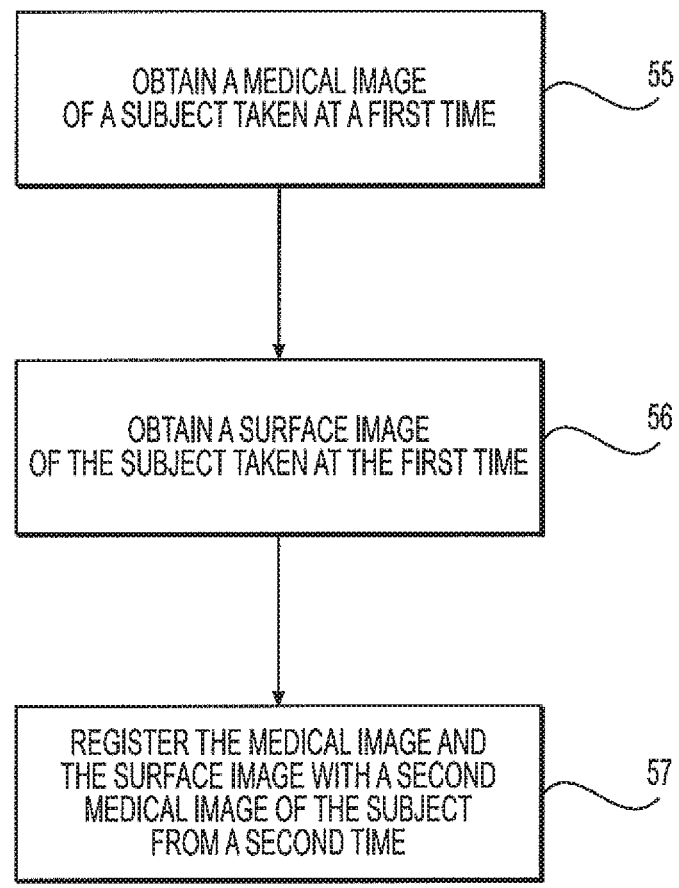
FIG. 4B is a flow chart portraying an exemplary imaging method, according to various embodiments of the present disclosure.

FIG. 4B depicts a similar method as described in reference to FIG. 4A, except that in the method of FIG. 4B, alignment or registration of the medical image and the surface image from the first time occurs simultaneously with registration of the second medical image from a second time. Accordingly, a medical image of a subject at a first time is obtained (step 55), a surface image of the subject at the first time is obtained (step 56), and then the medical image, the surface image, and a second medical image of the subject from a second time are registered together (step 57).

Figure 5:
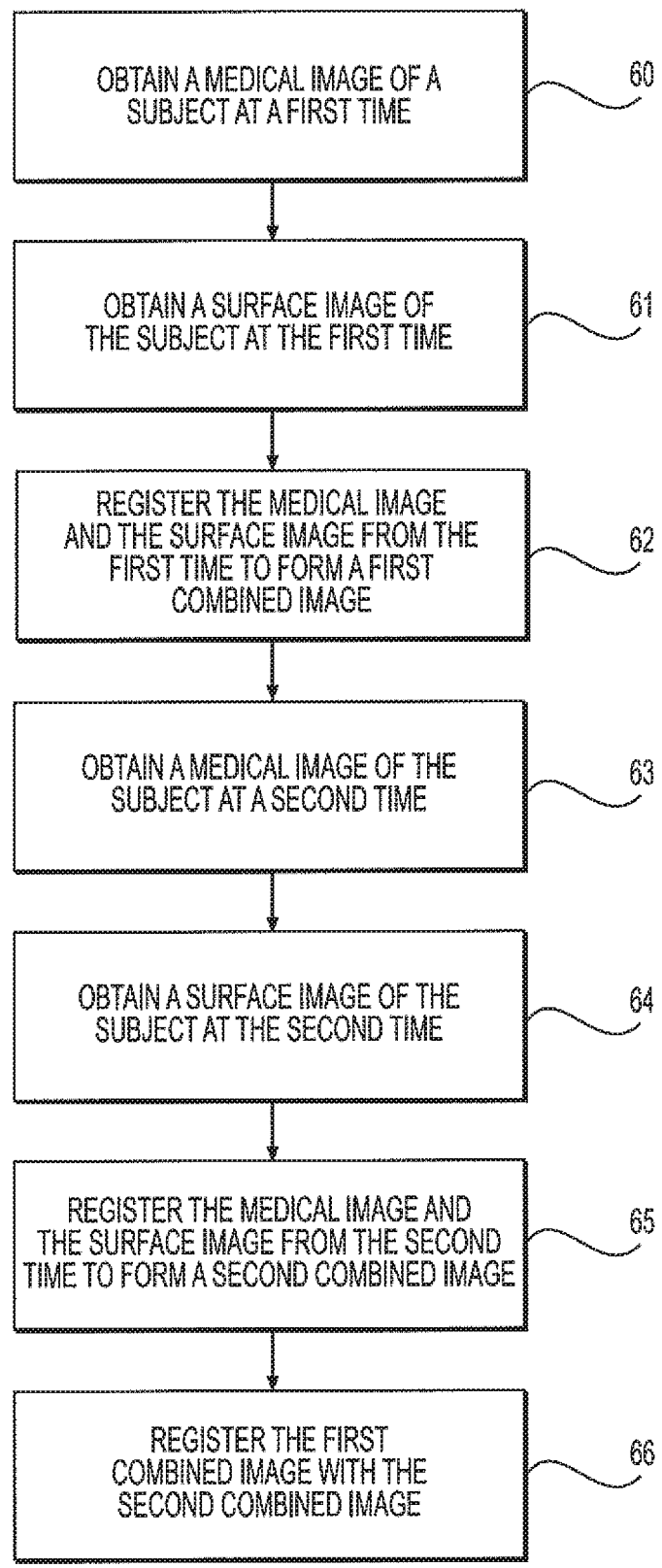
FIG. 5 is a flow chart portraying an exemplary imaging method, according to various embodiments of the present disclosure.

FIG. 5 depicts another exemplary method of the disclosure. In the embodiment of FIG. 5, a medical image of a subject is obtained at a first time, step 60. The medical image may include one or more of a CT, CBCT, MR, ultrasound, X-ray, PET, or SPECT image, or any other suitable type of medical imaging. The medical image may be taken by an image acquisition system incorporated into a radiation delivery device, or may be taken by an image acquisition system that is separate from a radiation delivery device. The medical image may be a 2D or a 3D image, for example. The first time may be prior to, during, or after a radiotherapy treatment fraction, for example, or before, during or after the delivery of radiotherapy during a fraction. The first time may alternatively have occurred during a prior fraction or during treatment planning or patient preparation. Also at the first time, a surface image of the subject may be obtained (step 61), for example, using a surface imaging camera system, which may include one or more cameras. The surface image may be a 2D or a 3D image, for example. The surface imaging camera system may be separate from a radiation delivery device or may be incorporated into a radiation delivery device.

Once the medical image and the surface image are obtained, the medical image and the surface image from the first time may be aligned or registered with each other to form a first combined image, step 62. The combined image may include one or more data points or other non-image information to indicate the position of the surface image and/or medical image in the combined image. In some embodiments, deformable registration may be used to register the surface image and the medical image. Registration may be performed using any suitable image processing technology, which may be uploaded and/or stored on any suitable processor, as described further below.

A medical image of the subject at a second time may also be obtained, step 63, and a surface image of the subject may be obtained at the second time, step 64. The second time may be different than the first time. In some embodiments, the second time may be a different time during the same treatment fraction. In some embodiments, the first time may be before, during, or after the delivery of radiotherapy during a treatment fraction, and the second time may be before, during, or after the delivery of radiotherapy during the same treatment fraction, a previous treatment fraction, a later treatment fraction, or a treatment planning or patient preparation stage. It is also noted that the first time does not need to come before the second time; indeed, the second time may precede the first time. The terms 'first' and 'second' simply denote two, separate times.

The medical image and the surface image from the second time may be registered to form a second, combined image, step 65. The first, combined image may then be registered with the second, combined image, step 66. In some embodiments, deformable registration may be used to register the surface image and the medical image and/or to register the first combined image with the second combined image. Registration may be performed using any suitable image processing technology, which may be uploaded and/or stored on any suitable processor, as described further below.

In some embodiments, the method of FIG. 5 may be used for patient tracking and/or adaptive tracking, e.g., for tracking movement of a patient and/or a region of interest before, during, and/or after the administration of radiotherapy during a fraction or across fractions. For example, the medical images may be MR or CBCT images taken before, during, and/or after radiotherapy treatment. Each MR or CBCT image may be paired with and registered with a surface image taken at the same time as the MR or CBCT image. The combined registered medical and surface images taken at the same time can then be used to compare with other surface/medical image pairs to assess movement of the patient and/or the target region. In some embodiments, if movement beyond a threshold level is detected, then radiotherapy treatment may be altered and/or stopped.

In regards to exemplary methods of the embodiments, medical images, whether taken at a first time or a second time, may include, e.g., one or more of a CT, CBCT, MR, ultrasound, X-ray, PET, or SPECT image, or any other suitable type of medical imaging. Surface images, whether taken at a first time or a second time, may include one or more images taken with an optical, infrared, thermal, stereoscopic (e.g., RGB stereoscopic), time-of-flight, or structured-light surface imaging system, or may be taken using Kinect technology, as described above. The medical images and surface images may be 3D or 2D.

Although FIGS. 4A, 4B, and 5, described herein, refer to "obtaining" a medical image and/or a surface image, it is contemplated that the verb "obtaining" may be replaced with "receiving" such an image. For example, a radiotherapy system may both obtain and register the images, performing each of the listed steps, or an image processor may simply receive images obtained by a separate medical and/or surface imaging system (whether those imaging systems are separate or integrated with each other), and may then register the received images. Accordingly, it is possible that images taken at a first time and/or taken at a second time are received by an image processor for registration and the method may not include active obtaining of the images.

As discussed herein, embodiments of the disclosure may be performed using any suitable equipment. Accordingly, surface imaging systems (including, e.g., optical, infrared, thermal, stereoscopic (e.g., RGB stereoscopic), time-of-flight, structured-light, Kinect technology, or other imaging systems) may be used in conjunction with—or incorporated into—any suitable medical imaging system and may be used to perform the disclosed methods. Some exemplary medical imaging systems with which surface imaging systems may be used have been described in reference to FIGS. 2, 3, 6, and 7.

Figure 6:
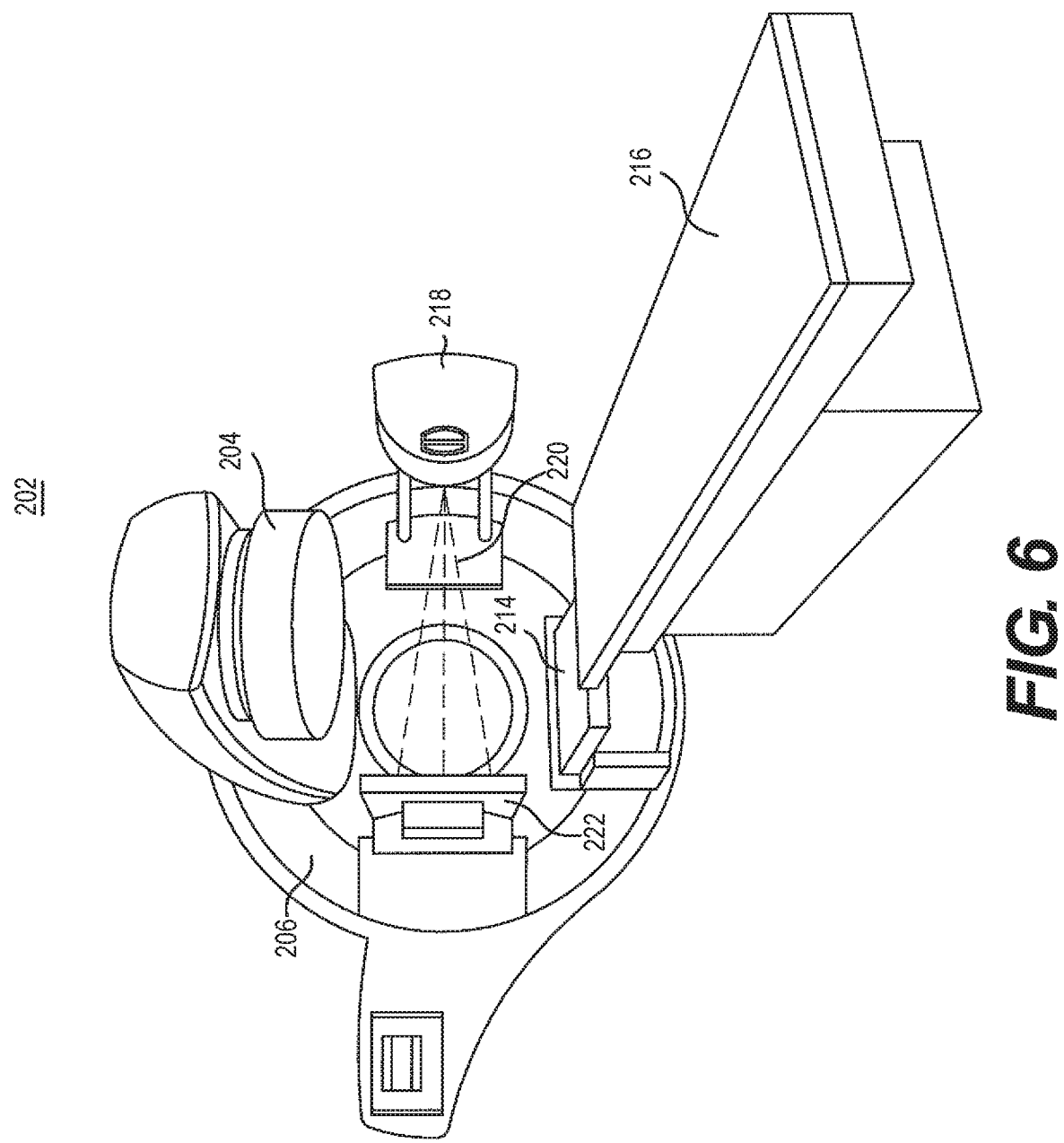
FIG. 6 illustrates a combined radiation therapy system and imaging system.

FIG. 6 illustrates an exemplary radiation therapy device 202 that may combine a linac and an imaging system. For example, the device of FIG. 6 may include a CT imaging system. The CT imaging system may include an imaging X-ray source 218, which may provide X-ray energy in a kiloelectron-Volt (keV) energy range. The imaging X-ray source 218 may provide a fan-shaped and/or a conical beam 220 directed to an imaging detector 222, such as a flat panel detector. Radiation therapy device 202 may be similar to radiation therapy device 102 described in relation to FIG. 3; for example, it may include a radiation therapy output 204, a gantry 206, a platform 216, and a flat panel detector 214. X-ray source 218 may provide a comparatively lower-energy X-ray diagnostic beam for imaging.

In the illustrative embodiment of FIG. 6, radiation therapy output 204 and X-ray source 218 may be mounted on the same rotating gantry 206, rotationally-separated from each other by 90 degrees. In another example, two or more X-ray sources may be mounted along the circumference of gantry 206, for example, each may have its own detector arrangement to provide multiple angles of diagnostic imaging concurrently. Similarly, multiple radiation therapy outputs 204 may be provided.

The illustrations of radiation therapy devices presented herein are not limiting with regard to this disclosure. Other known devices such as a device that combines a radiation therapy device and an imaging system, such as a nuclear MR imaging system (e.g., known in the art as an MR-Linac) are consistent with the disclosed embodiments. Such a device e.g., a magnetic resonance image linac (MRIL) machine, may be able to acquire real-time MR images of the patient during the administration of treatment.

Figure 7:
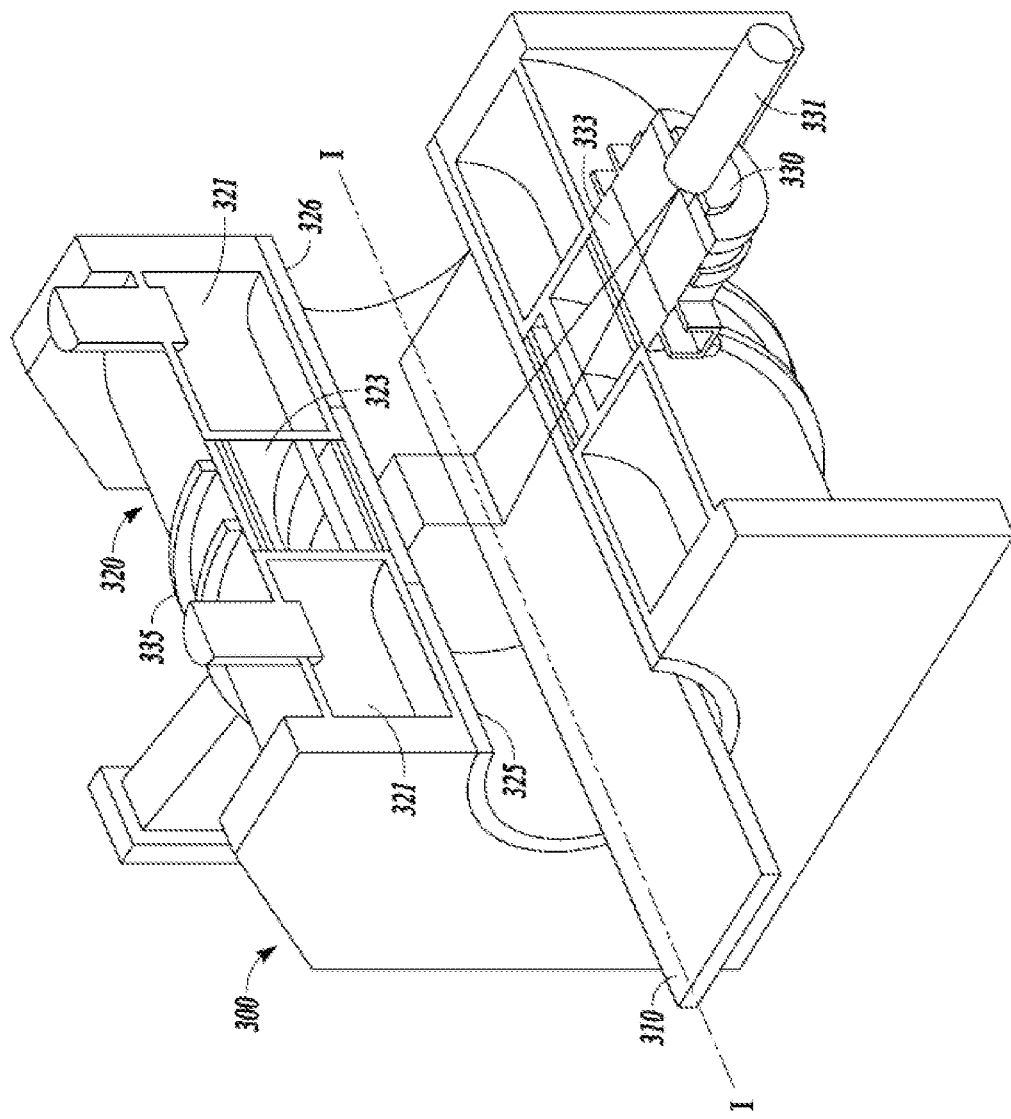
FIG. 7 illustrates a partial cut-away view of a combined radiation therapy system and imaging system.

FIG. 7 depicts an exemplary radiation therapy system 300 that may combine a radiation therapy device and an imaging system, such as a nuclear MR imaging system (e.g., known in the art as an MR-Linac) consistent with the disclosed embodiments. As shown, system 300 may include a couch 310, an image acquisition device 320, and a radiation delivery device 330. System 300 may be configured to deliver radiation therapy to a patient, e.g., in accordance with a radiotherapy treatment plan. In some embodiments, image acquisition device 320 may correspond to image acquisition device 32 in FIG. 2, which may acquire origin images of a first modality (e.g., MR image) or destination images of a second modality (e.g., CT image). Couch 310 may support a patient (not shown) during a treatment session. In some implementations, couch 310 may move along a horizontal, translation axis (labelled "I"), such that couch 310 may move the patient resting on couch 310 into and/or out of system 300. Couch 310 may also rotate around a central vertical axis of rotation, transverse to the translation axis. To allow such movement or rotation, couch 310 may have motors (not shown) enabling couch 310 to move in various directions and to rotate along various axes. A controller (not shown) may control these movements or rotations in order to properly position the patient according to a treatment plan.

In some embodiments, image acquisition device 320 may include an MRI machine used to acquire 2D or 3D MR images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position may be determined. Gradient coils 325 and 326 may be positioned around a common central axis with magnet 321, and may be displaced along that central axis. The displacement may create a gap, or window, between coils 325 and 326. In embodiments in which magnet 321 also includes a central window 323 between coils, the two windows may be aligned with each other.

Radiotherapy device 330 may include a source of radiation 331, such as an X-ray source or a linac, and a multi-leaf collimator (MLC) 333. Radiotherapy device 330 may be mounted on a chassis 335. One or more chassis motors (not shown) may rotate chassis 335 around couch 310 when couch 310 is inserted into the treatment area. In an embodiment, chassis 335 may be continuously rotatable around couch 310, when couch 310 is inserted into the treatment area. Chassis 335 may also have an attached radiation detector (not shown), for example, located opposite to radiation source 331 and with the rotational axis of chassis 335 positioned between radiation source 331 and the detector. Further, radiotherapy device 330 may include control circuitry (not shown) used to control, for example, one or more of couch 310, image acquisition device 320, and/or radiotherapy device 330.

FIGS. 3, 6, and 7 generally illustrate examples of radiation therapy devices configured to provide radiotherapy treatment to a patient, including a configuration in which a radiation therapy output may be rotated around a central axis (e.g., an axis "A"). Other radiation therapy output configurations may also be used. For example, a radiation therapy output may be mounted to a robotic arm or manipulator having multiple degrees of freedom. In yet another example, the radiation therapy output may be fixed, e.g., in a region laterally separated from the patient, and a platform supporting the patient may be used to align a radiation therapy isocenter with a specified target locus within the patient.

The many features and advantages of the present disclosure are apparent from the detailed specification, and thus, it is intended by the appended claims to cover all such features and advantages of the present disclosure that fall within the true spirit and scope of the disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. An image processing system comprising:
an image processor circuit configured to:
receive a medical image of a region of a subject's body taken at a first time;
receive a surface image of an exterior portion of the region of the subject's body taken at the first time, wherein the first time occurs during a radiotherapy treatment fraction;
receive a medical image of the region of the subject's body taken at a second time, wherein the second time occurs during a planning stage;
register the medical image taken at the first time and the surface image taken at the first time to form a combined image, and then register the combined image with the medical image taken at the second time to form a combined registered image, wherein the combined registered image includes one or more data points or other non-image information to indicate a position of the surface image taken at the first time and the position of the medical image taken at the first time.

2. The system of claim 1, wherein registering the medical image taken at the first time and the surface image taken at the first time to form a combined image includes using deformable registration.

3. The system of claim 1, wherein the second time precedes the first time.

4. The system of claim 1, wherein the medical image taken at the second time is a planning computed tomography image.

5. The system of claim 1, wherein the medical image taken at the first time is either a magnetic resonance image or a cone-beam computed tomography image.

6. The system of claim 1, wherein the image processor circuit is further configured to obtain the medical image at the first time and obtain the surface image at the first time.

7. The system of claim 1, wherein the surface image is one of an optical image, an infrared image, a thermal image, or a stereoscopic image.

8. The system of claim 1, wherein the medical image taken at the second time includes at least part of the exterior portion of the region of the subject's body.

9. A computer-implemented image processing method comprising:
receiving a first medical image of a region of a subject's body taken at a first time;
receiving a first surface image of an exterior portion of the region of the subject's body at the first time, wherein the first time occurs during a radiotherapy treatment fraction;
registering the first medical image and the first surface image to form a first combined image;
receiving a second medical image of the region of the subject's body taken at a second time;
receiving a second surface image of the exterior portion of the region of the subject's body at the second time, wherein the second time occurs during a planning stage;
registering the second medical image and the second surface image to form a second combined image; and
registering the first combined image and the second combined image to form a combined registered image, wherein the combined registered image includes one or more data points or other non-image information to indicate a position of the first surface image taken at the first time and the position of the first medical image taken at the first time.

10. The method of claim 9, wherein the first medical image and the second medical image are either magnetic resonance images or cone-beam computed tomography images.

11. The method of claim 9, wherein the first surface image and the second surface image are an optical image, an infrared image, a thermal image, or a stereoscopic image.

12. A non-transitory computer-readable medium storing instructions that, when executed by a processor, cause the processor to perform an image processing method, the method comprising:
receiving a medical image of an interior region of a subject's body taken at a first time;
receiving a surface image of an exterior portion of the interior region of the subject's body taken at the first time, wherein the first time occurs during a radiotherapy treatment fraction;
receiving a medical image of the subject's body taken at a second time, wherein the second time occurs during a planning stage; and
registering the medical image taken at the first time and the surface image taken at the first time to form a combined image, and then register the combined image with the medical image taken at the second time using deformable registration to form a combined registered image, wherein the combined registered image includes one or more data points or other non-image information to indicate a position of the surface image taken at the first time and the medical image taken at the first time.

13. The method of claim 12, wherein the surface image is one of an optical image, an infrared image, a thermal image, or a stereoscopic image.

14. The method of claim 12, wherein the medical image taken at the second time is a planning computed tomography image, and the medical image taken at the first time is either a magnetic resonance image or a cone-beam computed tomography image.

15. The method of claim 14, wherein the planning computed tomography image also includes at least some of the exterior portion of the interior region of the subject's body.

* * * * *